United States Patent [19]

Spielvogel et al.

[11] Patent Number: 5,434,143
[45] Date of Patent: Jul. 18, 1995

[54] PHARMACEUTICAL COMPOSITIONS COMPRISING PHOSPHITE-BORANE COMPOUNDS

[75] Inventors: Bernard F. Spielvogel, Raleigh; Anup Sood, Durham, both of N.C.

[73] Assignee: Boron Biologicals, Inc., Raleigh, N.C.

[21] Appl. No.: 326,008

[22] Filed: Oct. 19, 1994

Related U.S. Application Data

[60] Continuation of Ser. No. 148,986, Nov. 8, 1993, abandoned, which is a division of Ser. No. 908,975, Jul. 6, 1992, Pat. No. 5,260,427, which is a continuation-in-part of Ser. No. 701,682, May 10, 1991, Pat. No. 5,143,907.

[51] Int. Cl.$^6$ .............................................. A61K 31/69
[52] U.S. Cl. ......................................... 514/64; 558/72
[58] Field of Search ........................................... 514/64

[56] References Cited

U.S. PATENT DOCUMENTS 3,104,253  9/1963  Reetz et al. ............................ 558/72
3,119,853  1/1964  Reetz ............................... 558/72 X

*Primary Examiner*—Mary C. Lee
*Assistant Examiner*—Michael G. Ambrose
*Attorney, Agent, or Firm*—Fran S. Wasserman; Steven J. Hultquist

[57] ABSTRACT

The phosphite-borane compounds of the present invention correspond to the formula

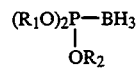

where
  $R_1$ is independently selected from H, $C_1$-$C_{20}$ alkyl, alkylaryl, aryl, trialkylsilyl, with the proviso that both $R_1$ groups cannot simultaneously be $H_1$, and
  $R_2$ is selected from H, a monovalent cation such as $Li^+$, $Na^+$, $K^+$, $NH_4^+$, $N(R_3^+)_4$, where $R_3$ is independently selected from H, $C_1$-$C_{20}$ alkyl.

The phosphite-borane compounds of the present invention are bioactive in character, variously exhibiting anti-tumor, anti-inflammatory, and hypolipidemic activity. Also disclosed are various synthetic methods for making such phosphite-borane compounds, and for formulating same in unit dosage forms as well as other pharmaceutically and pharmacologically acceptable formulations.

4 Claims, No Drawings

PHARMACEUTICAL COMPOSITIONS COMPRISING PHOSPHITE-BORANE COMPOUNDS

GOVERNMENT RIGHTS IN INVENTION

The invention may be used by the U.S. Government for Governmental purposes without the payment of royalties to the inventors.

CROSS-REFERENCE TO RELATED APPLICATION

This is a Continuation of application Ser. No. 08/148,986 filed Nov. 8, 1993, abandoned, which in turn is a Divisional of Application Ser. No. 07/908,975, filed Jul. 6, 1992, and issued Nov. 9, 1993 as U.S. Pat. No. 5,260,427, which in turn is a Continuation-in-Part of application Ser. No. 07/701,682 filed May 10, 1991 and issued on Sep. 1, 1992 as U.S. Pat. No. 5,143,907.

BACKGROUND OF THE INVENTION

1. Field of the Invention

The present invention relates to phosphite-borane derivatives with nucleoside substituents that exhibit antineoplastic, anti-hyperlipidemic, and anti-inflammatory activity.

2. Description of the Related Art

A. Lewis Base-borane Compounds

Various boron-containing compounds have previously been shown to exhibit therapeutic biological activity. For example, amine-borane compounds such as amine.$BH_2COOH$, amine.$BH_2COOMe$ and amine.$BH_2CONHR$ have been demonstrated to exhibit antitumor, anti-inflammatory and hypolipidemic activities. Additionally, phosphite-borane compounds have been used in hydroboration under mild conditions (Pelter, A., et al, *J. Chem. Soc. Chem. Commun.* 1981, 1014). Since the first reports of phosphite-borane compounds and their properties (Reetz, T., *J. Am. Chem. Soc.* 1960, 82, 5039), very few phosphite-borane compounds have been synthesized and/or had their properties investigated (Das, M. K., et al, *Synth. React. Inorg. Met. Org. Chem.* 1986, 16, 67; Martin, D. R. et al; Pennington, B. T., *J. Inorg. Nucl. Chem.* 1978, 40, 9; and Mutterties, E. L., "The Chemistry of Boron and its Compounds," Wiley, New York, 1967).

Generally, phosphite-borane derivatives may be considered as analogs of alkylphosphates, $(RO)_3P=O$ vs. $(RO)_3PBH_3$, as well as analogs of alkylphosphonates, e.g., $(RO)_2P(O)CH_3$ vs. $(RO)_2P(O)BH_3$, or $(RO)_2P(O)CH_2X$ vs. $(RO)_2P(O)BH_2X$, wherein R is alkyl and X is heteroatom substituent. Since phosphate and phosphonate groups are present in a variety of biologically important molecules, e.g., DNA, RNA, phospholipids, aminophosphonates, etc., their boron-containing analogs may prove useful as biomolecular probes and as potential therapeutic agents.

Additionally, several synthetic phosphonates, e.g., phosphonoacetic acid, phosphonoformic acid, etc., have been found to possess significant antiviral activity (Mayer, R. F., et al, *Antimicrob. Agents Chemother.* 1976, 9, 308; Oberg, B., *Pharmac. Ther.*, 1983, 19, 387; and Clerq, E. D., *J. Med. Chem.* 1986, 29, 1561). This antiviral activity coupled with the established pharmacological activity of amine-borane derivatives makes phosphite-borane derivatives potentially significant as a class of bioactive compounds.

B. Modified Nucleotides

Ribo- and deoxyribonucleoside 5'-mono-, di-, and triphosphates play a central role in the metabolism of nucleic acids, one of the most important polymer molecules of living systems. It has long been realized that chemically modified analogs of nucleoside mono-, di-, and tri-phosphates may be useful tools to probe different steps of nucleic add metabolism. It has also been recognized that they may have valuable chemotherapeutic properties. Therefore, synthesis and study of nucleotide analogs has long been in the center of interest.

Several modifications of the phosphate group have been carried out and the derivatives are shown in Table 1 below. These derivatives mainly involve phosphorothioates (Eckstein, F. *Angew Chem. Int. Ed. Engl.* 1983, 22, 423–439 and references therein, Eckstein, F. *Ann. Rev. Biochem.* 1985, 54, 367–402 and references therein, Ludwig, J.; Eckstein, F. *J. Org. Chem.* 1989, 54, 631–635, and Ludwig, J.; Eckstein, F. *J. Org. Chem.* 1991, 86, 5860–5865), phosphorodithioates (Ludwig, J.; Eckstein, F. *J. Org. Chem.* 1991, 56, 1777–1783), phosphoramidates (Chambers, R. W.; Moffatt, J. G., *J. Am. Chem. Soc.* 1958, 80, 3752–3756; Chambers, R. W. et al, ibid, 1960, 82, 970–975; Moffatt, J. G.; Khorana, H. G., ibid, 1961, 83, 649–658; Cramer, F. et al, *Chem. Ber.* 1961, 94, 1612–1621; Schaller et al. ibid, 1961, 94, 1621–1633; Cramer, F.; Neunhoffer, H., ibid, 1962, 95, 1664–1669; Simoncsits, A.; Tomasz, J., *Tetrahedron Lett.* 1976, 3995–3998; Tomasz, J.; Simoncsits, A., *J. Carbohydrates—Nucleosides—Nucleotides* 1978, 5, 503–522; Tomasz, J., *Nucleosides & Nucleotides* 1983, 2, 63–79; Bakina, G. T. et al. *Bioorg. Khim,* 1975, 1, 611–615 and Zarytora, V. F. et al, ibid 1975, 1, 793–798), phosphonates (Anand, N.; Todd, A. R., *J. Chem. Soc.* 1951, 1867–1872; Engel, R. *Chem. Revs.* 1977, 77, 349–367 and references therein ad Myers, T. C.; Simon, N. L., *J. Org. Chem.* 1985, 30, 443–446), phosphorofluoridates (Wittmann, R., *Chem. Ber.* 1963, 96, 771–779, Johnson, P. W. et al, *Nucleic Acids Res.* 1975, 2, 1745–1749; Staley, B.; Yount, R. G., *Biochemistry* 1972, 11, 2863–2871 and Eckstein, F. et al, ibid, 1975 114, 5225–5232), phosphites or H-phosphonates (Corby, N. S. et al, *J. Chem. Soc.*, 1952, 3669–3674, Sir Todd, A., ibid, 1961, 2316–2320 and Holy, A. et al, *Cell. Czech. Chem. Commun.* 1965, 30, 1635–1641), phosphorazidates (Chladek, S. et al., *Biochemistry* 1977, 16, 4312–4319), phosphonoselenoates (Sekine, M.; Hata, T., *Tetrahedron Lett.* 1979, 801–802) and alkyl phosphates (Hoffmann, P. J.; Blakley, R. L., *Biochemistry* 1975, 14, 4804–4812.

TABLE 1

Structural formulae of nucleoside 5'-mono-, di- and triphosphates derivatised at the phosphorus

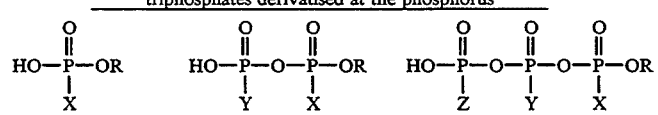

TABLE 1-continued

| X | Y | X | Z | Y | X |
|---|---|---|---|---|---|
| 1 $S^-$ | 2 $O^-$ | $S^-$ | 4 $O^-$ | $O^-$ | $S^-$ |
| 10 $NH_2$, $NHR'$ or $NR'_2$ | 3 $S^-$ | $O^-$ | 5 $O^-$ | $S^-$ | $O^-$ |
| 13 $CH_3$ or $CH_2R'$ | 14 $CH_3$ | $O^-$ | 6 $S^-$ | $O^-$ | $O^-$ |
| 15 F | 16 F | $O^-$ | 7 $O^-$ | $S^-_3$ | $S^-$ |
| 18 H | 20 $N_3$ | $O^-$ | 8 $S^-$ | $O^-$ | $S^-$ |
| 19 $N_3$ | | | 11 $O^-$ | $O^-$ | $NH_2$ |
| 22 $Se^-$ | | | 12 $R'NH$ | $O^-$ | $O^-$ |
| | | | 17 F | $O^-$ | $O^-$ |
| | | | 21 $N_3$ | $O^-$ | $O^-$ |
| | | | 23 $R'O$ | $O^-$ | $O^-$ |

$$\text{HO}\overset{O}{\underset{O^-}{\overset{\|}{P}}}-O-\overset{O}{\underset{O^-}{\overset{\|}{P}}}-O-\overset{S}{\underset{S^-}{\overset{\|}{P}}}\text{OR}$$

9

Derivatization at the phosphorus moiety by replacing a non-bridging oxygen atom confers chirality on the P1 phosphorus of compounds 2, 4, 7, 8, and 11 as well as P2 of 5 and 7. As a result of the chirality of the sugar residue, nucleotide 5'-di- and triphosphate derivatives 2, 4, 5, 7, 8 and 11 formed during chemical synthesis exist as pairs of phosphorus, Rp and Sp, diastereoisomers. The chirality of phosphorus renders these derivatives suitable tools for studying the stereochemistry of enzyme catalyzed reactions. The diastereoisomers, however, have to be separated, since the diastereoisomeric purity of the substrate is an essential prerequisite for stereochemical studies.

Taking into consideration the chirality of phosphorus, it is not surprising that, among the nucleoside 5'-mono-, di-, and triphosphate analogs listed in Table 1 above, the thiophosphates have found widespread applications in biochemistry and molecular biology. Nucleoside phosphorothioate diastereoisomers have been used to determine the stereochemical course of numerous enzyme catalyzed nucleotidyl and phosphoryl transfer reactions (Eckstein, F., *Angew Chem. Int. Ed. Engl.* 1983, 22, 423–439 and references therein and Eckstein, F. *Ann. Rev. Biochem.* 1985, 54, 367–402 and references therein). The stereochemical outcome of an enzymic reaction, i.e., whether it proceeds with inversion or retention of configuration at phosphorus, is an informative criterion about the presence or absence of a covalent enzyme intermediate. The Sp diastereoisomers of 4, as substrates of RNA and DNA polymerases, have successfully been employed for sequencing (Gish, G.; Eckstein, F., *Science,* 1988, 240, 1520–1522 and Nakamaye, K. L. et al., *Nucleic Acids Res.* 1988, 16, 9947–9959), oligonucleotide-directed mutagenesis (Nakamaye, K. L.; Eckstein, F., *Nucleic Acids Res.,* 1986, 14, 9679–9698 and Sayers, J. R. et al, ibid, 1988, 16, 791–802), and the labeling of the hybridization probes (Haase, A. T. et al, *Science* 1985, 227, 189–192 and Bahmanyar, S. et al, *Science,* 1987, 237, 77–80). Triphosphate derivatives 6 are also substrates for polymerases (Smith, M. M. et al, *Biochemistry* 1978, 17, 493–500). Many enzymes show strong preference for either the Sp or Rp diastereoisomer of triphosphates 4 and 5. For example, guanine nucleotide-binding proteins (G-proteins) which are implicated in signal transduction pathways (Bourne, H. R. et al, *Nature* 1990, 348, 125–132), transducin (the G-protein involved in vision) has a stronger affinity for the (Sp)-guanosine 5'-O-(2-thiotriphosphate). On the other hand, the G-protein responsible for the oscillatory release of $Ca^{2+}$ ions in most cells is preferentially activated by the (Rp)-diastereoisomer (von zur Muhlen, R.; Eckstein, F.; Penner, R. *Proc. Acad. Sci. U.S.A.* 1991, 88, 926–930). The stereoselectivity of the enzymes can be reversed by changing the metal cation necessary for the enzyme action from a hard to a soft one (Armstrong, V.; Eckstein, F., *Eur. J. Biochem.,* 1976, 70, 33–38).

Nucleoside-boranophosphates and boranophosphoramidates (phosphite-borane compounds), the compounds of the present invention, may be considered as analogs of corresponding phosphates or thiophosphates, where the oxygen or sulfur has been replaced with a borane substituent. These derivatives have similar charges and thus resemble phosphates or phosphorothioates.

On the other hand, differences are expected between boranophosphates and thiophosphates in reactivity, hydrogen bonding and metal ion chelating ability which may be a determinant for enzyme reactions. Consequently, it seems reasonable to suppose that boranophosphates may find similar and, at the same time, complementary applications to thiophosphates 1–6. Our initial results support this supposition.

The thymidine 5'-O-(1-boranotriphosphate) can substitute for thymidine 5'-triphosphate (dTTP) in the extension of a deoxyribo 17-mer primer by Sequenase, a modified T7 DNA polymerase, using a 25-mer template containing one 2'-deoxyadenosine residue. No detectable pause in polymerization was found at the dTTP incorporation site. These findings suggest that thymidine 5'-0-(1-boranotriphosphate), possibly one of the two phosphorus diastereoisomers like the (Sp) diastereoisomer of the analogous thiotriphosphates 4(Burgers, P. M. J.; Eckstein, F., *J. Biol. Chem.* 1979, 254, 6889–6893 and Romaniuk, P. J.; Eckstein, F., ibid 1982, 257, 7684–7688) is a substrate for polymerases.

It was also observed that acid phosphatase from sweet potato (EC 3.1.3.2) and 5'-nucleotidase from *Crotalus adamanteus* venom (EC 3.1.3.5) completely hydrolyses thymidine 5'-boranophosphate to thymidine. On the other hand, thymidine 5'-boranophosphate is a very poor substrate (or an inhibitor) of alkaline phosphatase from *Eschrichia coli* (EC 3.1.3.1). The analogous thiophosphate, thymidine 5'-thiophosphate, is a competitive inhibitor of both acid and alkaline phosphatases. The fact that thymidine 5'-boranophosphate is a substrate of acid phosphatase, while thymidine 5'-thiophosphate is a competitive inhibitor of the same enzyme, is remarkable and demonstrates the potential for the complimentary use of boranophosphates and thiophosphates to study the details of the mechanism of enzymic reactions.

In addition to molecular biology studies, modified nucleosides and nucleotides have demonstrated considerable pharmacological activity in the antiviral and antitumor areas (Mitsuya, H. Broder, S., *Proc. Natl.*

*Acad. Sci. USA,* 1986, 83, 1911–1915; Mitsuya, H. et al, *Proc. Natl. Acad. Sci. USA* 1985, 82, 7096–7100; Lin, T. S. et al, *J. Med. Chem.,* 1988, 31, 336–340; Beauchamp, L. M. et al, *J. Med. Chem.* 1988, 31, 144–149; Remy, R. J., Secrist III, J. A., *Nucleosides Nucleotides* 1985, 4, 411–427; Prusoff, W. H., Ward, D. C., *Biochem. Pharmacol.,* 1976, 25, 1233–1239; Marquez, V. E. et al, *J. Med. Chem.* 1988, 31, 1687–1694; Lin, T.-S., Prusoff, W. H., *J. Med. Chem.* 1978, 21, 109–112; Johnson, F. et al, *J. Med. Chem.* 1984, 27, 954–958; Secrist et al, *J. Med. Chem.* 1988, 31, 405–410; Farquherz, D., Smith, R., *J. Med. Chem.* 1985, 28, 1358–1361; Hunston, R. H. et al, *J. Med. Chem.* 1984, 27, 440–444; Farquher, D. et al, *J. Med. Chem.* 1983, 26, 1153–1158; McGuigan et al, *Nucleic Acids Res.* 1989, 17, 6065–6075; McGuigan et al, *Nucleic Acids Res.* 1989, 17, 10171–10177; Colin, B. et al, *Nucleic Acids Res.* 1989, 17, 7195–7201 and Lambert et al, *J. Med. Chem.* 1989, 32, 367–374). Thus, phosphite-boranes with nucleoside substituents may combine the pharmacological properties of Lewis-base-borane compounds and those of modified nucleosides to give superior therapeutic agents.

While it is clear that considerable potential exists for the utility of phosphite-borane derivatives with nucleoside substituents as biomolecular probes and therapeutic agents, it is equally clear that not much effort has been focused on exploiting this potential. The present invention arose from our ongoing research into boron analogs of biomolecules potentially useful as probes and therapeutic agents.

It therefore is an object of the present invention to provide new phosphite-borane derivatives including active antineoplastic, anti-hyperlipidemic, and anti-inflammatory agents.

It is another object of the present invention to provide new processes for synthesizing phosphite-borane derivatives exhibiting antineoplastic, anti-hyperlipidemic, and anti-inflammatory activity.

Other objects and advantages will be more fully apparent from the ensuing disclosure and appended claims.

SUMMARY OF THE INVENTION

The phosphite-borane compounds of the present invention comprise a category of phosphite-borane compounds within the broad scope of the phosphite-borane compounds of our prior copending U.S. application Ser. No. 07/701,682 filed May 10, 1991, wherein the phosphite moiety substituents comprise nucleosidyl substituent. An additional category represents simple phosphite-BH$_3$ compounds where phosphite is a mono- or dialkyl-phosphite or its salts. These compounds also possess significant antitumor, anti-hyperlipidemic and anti-inflammatory activities. In addition, these compounds are useful for studying enzymatic processes at the molecular level.

The phosphite-borane compounds of the present invention correspond to compounds of the following general categories:

a. A phosphite-borane compound corresponding to the formula

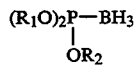

where:

R$_1$ is independently selected from H, C$_1$–C$_{20}$ alkyl, alkylaryl, aryl, and trialkylsilyl, with the proviso that both R$_1$ groups cannot simultaneously be H$_1$; and R$_2$ is selected from H, and a monovalent cation such as Li$^+$, Na$^+$, K$^+$, NH$_4^+$, and N(R$_3^+$)$_4$, where R$_3$ is independently selected from H, C$_1$–C$_{20}$ alkyl.

b. A phosphite-borane compound corresponding to the general formula

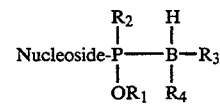

where:

nucleoside is a natural or synthetic (e.g. ribo-, deoxyribo-, dideoxyribo-, arabino-, xylo, acyclic, carbocyclic, oxetanocin, etc.) nucleoside connected to the phosphorus via one of its hydroxyl oxygens;

R$_1$ is selected from H, alkyl, aryl, alkylaryl, monovalent metal ions, and an ammonium cation;

R$_2$ is selected from OR$_1$, where R$_1$ is as above, PO$_4^{2-}$, P$_2$O$_7^{3-}$, OP(O)(OR$_5$)$_2$, OPO$_3$(OR$_5$)$_3$, and N(R$_5$)$_2$, where R$_5$ is independently selected from H, C$_1$–C$_{10}$ linear or branched alkyl, and aryl;

R$_3$ is selected from H, CN, COOH, carboxyl salts, COOR$_6$ and CONHR$_6$, wherein R$_6$ is selected from H, C$_1$–C$_{10}$ alkyl, alkylaryl and aryl; and R$_4$ is selected from H and C$_1$–C$_{10}$ alkyl.

c. A phosphite-borane compound corresponding to the formula

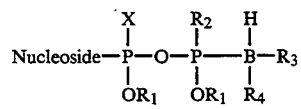

where:

nucleoside, R$_1$, R$_3$ and R$_4$ are the same as in category b;

X=O or BHR$_3$R$_4$;

R$_2$ is selected from OR$_1$, PO$_4^{2-}$, OP(O)(OR$_5$)$_2$ and N(R$_5$)$_2$, wherein R$_5$ is independently selected from H, C$_1$–C$_{10}$ linear or branched alkyl, and aryl.

d. A phosphite-borane compound corresponding to the formula

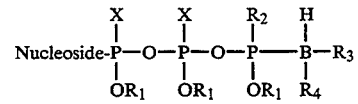

where:

Nucleoside, R$_1$, R$_3$ and R$_4$ are the same as in category b;

X is independently selected from O and BHR$_3$R$_4$;

R$_2$ is selected from OR$_1$ and N(R$_5$)$_2$, wherein R$_5$ is independently selected from H, C$_1$–C$_{10}$ linear or branched alkyl, and aryl.

Another aspect of the present invent-ion relates to processes for preparing phosphite-borane compounds of the above formulae. It has been discovered that phosphite-borane compounds of these types can be prepared i) from a nucleoside by boranophosphorylation in a multistep process, ii) from nucleoside substituted phosphites by boronation in a multistep process or iii) by condensation of a di- or mono-alkylphosphiteborane with a nucleoside. The final products generated by these processes, as well as the intermediate boronated products of the multistep processes, comprise phosphite-borane compounds of the present invention. The phosphite-borane compounds of class (a.) above may be prepared by hydrolysis of trialkylphosphite-boranes.

Yet another aspect of the present invention relates to the use of these compounds to treat tumors, inflammation and hyperlipidemia.

DETAILED DESCRIPTION OF THE INVENTION

The novel phosphite-borane derivatives of the present invention are a further development of the phosphite-borane compounds broadly disclosed in our prior copending application Ser. No. 07/701,682 filed May 10, 1991, in that in the phosphite-borane compounds of the present invent-ion, the in that the phosphite is connected to a nucleoside or, in the case of borane adducts of mono- or dialkyl-phosphites or their salts, the borane group represents $BH_3$.

The phosphite-borane compounds of the present invention correspond to the following general categories:

a. phosphite-borane compounds corresponding to the formula:

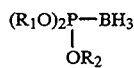

where:

$R_1$ is independently selected from H, $C_1$–$C_{20}$ alkyl, alkylaryl, aryl, and trialkylsilyl, with the proviso that both $R_1$ groups cannot simultaneously be $H_1$, and $R_2$ is selected from H, and a monovalent cation such as $Li^+$, $Na^+$, $K^+$, $NH_4^+$, $N(R_3^+)_4$, where $R_3$ is independently selected from H, and $C_1$–$C_{20}$ alkyl.

b. phosphite-borane compounds corresponding to the general formula

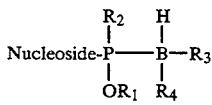

where:

Nucleoside is a natural or synthetic (e.g. ribo-, deoxyribo-, dideoxyribo-, arabino-, xylo, acyclic, carbocyclic, oxetanocin, etc.) nucleoside connected to the phosphorus via a hydroxyl oxygen;

$R_1$ is selected from H, alkyl, aryl, alkylaryl, monovalent metal ions, and an ammonium cation;

$R_2$ is selected from $OR_1$, where $R_1$ is as above, $PO_4^{2-}$, $P_2O_7^{3-}$, $OP(O)(OR_5)_2$, $OPO_3(OR_5)_3$, and $N(R_5)_2$, where $R_5$ is independently selected from H, $C_1$–$C_{10}$ linear or branched alkyl, and aryl;

$R_3$ is selected from H, CN, COOH, carboxyl salts, $COOR_6$ and $CONHR_6$, wherein $R_6$ is selected from H, $C_1$–$C_{10}$ alkyl, alkylaryl and an/l; and $R_4$ is selected from H and $C_1$–$C_{10}$ alkyl.

c. phosphite-borane compounds corresponding to the formula

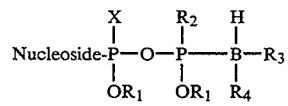

where:

Nucleoside, $R_1$, $R_3$ and $R_4$ are the same as in category b;

X=O or $BHR_3R_4$;

$R_2$ is selected from $OR_1$, $PO_4^{2-}$, $OP(O)(OR_5)_2$ and $N(R_5)_2$, wherein $R_5$ is independently selected from H, $C_1$–$C_{10}$ linear or branched alkyl, and aryl.

d. phosphite-borane compounds corresponding to the formula:

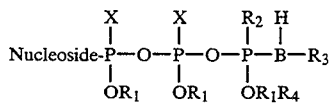

where:

Nucleoside, $R_1$, $R_3$ and $R_4$ are the same as in category b;

X is independently selected from O or $BHR_3R_4$;

$R_2$ is selected from $OR_1$ and $N(R_5)_2$, wherein $R_5$ is independently selected from H, $C_1$–$C_{10}$ linear or branched alkyl, and aryl.

In the phosphite-borane compounds of the foregoing formulae, the alkyl moiety, whether itself or as a part of alkylaryl or aryl radicals or ammonion ions, may either be linear or branched.

It is to be appreciated that the aliphatic and/or aromatic substituents referred to above may optionally be substituted with heteroatoms or otherwise further substituted, subject to the proviso that such further substitution does not preclude the utility of the resulting compound.

The nucleoside preferably is selected from a ribo-, deoxribo-, dideoxyribo-, arabino- or an acyclic-nucleoside; $R_1$ is selected from H, $C_1$–$C_{10}$ alkyl, monovalent-ions $Li^+$, $Na^+$, $K^+$, $NH_4^+$ and $(n-C_4H_9)_3NH^+$; $R_2$ is $OR_1$, $PO_4^{2-}$, $P_2O_7^{3-}$ or $(NR_5)_2$ where $R_5$ is independently selected from H or $C_1$–$C_5$ linear or branched alkyl; $R_3$ is selected from H, CN, COOH, $COOCH_3$ and $CONHC_2H_5$; and $R_4$ is H.

In a particularly preferred aspect, nucleoside is a ribo- or a deoxyribo nucleoside; $R_1$ is H, $CH_3$, $CH_2CH_3$ or $CH_2CH_2CN$; $R_2$ is $OR_1$, $PO_4^{2-}$, $P_2O_7^{3-}$ or $N(i-C_3H_7)_2$; $R_3$ is H, or CN; and $R_4$ is H.

Exemplary phosphite-borane derivatives of the present invention include the following:
Diethylphosphite-borane
Diethylphosphite-borane, sodium salt
Dibutylphosphite-borane, tetra-n-butylammonium salt
Ethyl(isopropyl)phosphite-borane, sodium salt
Dimethylphosphite-borane, ammonium salt
Mono-n-butylphosphite-borane, lithium salt
Mono-i-propylphosphite-borane
Monomethylphosphite-borane, sodium salt
Thymidine-5′-boranophosphate
2′-Deoxyadenosine-3′-boranophosphate
2′-Deoxyguanosine-5′-(N,N-diisopropyl)boranophosphoramidate
Thmidine-5′-O-(α-boranodiphosphate)
2′-Deoxycytidine-5′-O-(α-boranotriphosphate)
Cytidine-5′-O(α,β-diboranodiphosphate)

Guanosine-5'-O-(α,β-diboranotriphosphate)
Adenosine-5'-O-(α,γ-diboranotriphosphate)
Xanthosine-5'-O-(α,β,γ-triboranotriphosphate)
2'-Deoxyinosine-5'-O-(β-boranotriphosphate)
ara-Adenosine-5'-O-(α,γ-diboranotriphosphate)
Acyclovir-O-(β,γ-diboranotriphosphate)
Ribavirin-5'-O-(α,β-diboranodiphosphate)
Adenosine-2'-boranophosphate
Uridine-5'-O-(β-borano-β-diisopropylamino-β-{2-cyano}ethoxy-diphosphate)
2'-Deoxycytidine-5'-O-(β-borano-β-diisopropylamino-β-methoxy diphosphate
Guanosine-5'-boranophosphate
Uridine-2'-boranophosphate
Cordycepin-2'-boranophosphate
2'-Deoxycytidine-3'-boranophosphate
Adenosine-3'-boranophosphate
Cytidine-5'-(N,N-diisopropyl)boranophosphoramidate
Guanosine-5'-O-(α boranodiphosphate)
Ribavirin-5'-O(α-boranodiphosphate)
Thymidine-5'-O-(β-boranodiphosphate)
2'-Deoxyguanosine-5'-O-(α,β-diboranodiphosphate)
2'-Deoxyadenosine-5'-O-(α,β-diboranotriphosphate)
ara-Adenosine-5'-O-(α-boranotriphosphate)
2'-Deoxyinosine-5'-O-(α-boranotriphosphate)
Inosine-5'-O-(α,β-diboranotriphosphate)
Uridine-5'-O-(α,β-diboranotriphosphate)
2'-Deoxyuridine-5'-O-(α,γ-diboranotriphosphate)
2'-Deoxyxanthosine-5'-O-(γ-boranotriphosphate)
Adenosine-5'-O-(β-boranodiphosphate)
Uridine-2'-boranophosphate
Cytidine-2'-boranophosphate
2'-Deoxyadenosine-5'-O-(β,γ-diboranotriphosphate)
Guanosine-5'-O-(β,γ-diboranotriphosphate)
Thymidine-5'-O-(α,β,γ-triboranotriphosphate)
2'-Deoxyuridine-5'-O-(α,β,γ-triboranotriphosphate)

The present invention also comprises a method for preparing the compounds of the present invent, ion. Four distinct processes have been employed to synthesize the compounds of the present invention.

The first multistep process which may be used to produce phosphite-borane compounds of the present invention involves the following basic steps:

a. phosphitylation of a nucleoside, a nucleoside phosphate, a nucleoside-diphosphate, a nucleoside boranophosphate, a nucleoside α-boranodiphosphate, a nucleoside β-boranodiphosphate or a nucleoside-α,β-diboranodiphosphate.

b. transfer of boron from an appropriate Lewis base to the phosphoramidite intermediate, c. de-esterification, d. hydrolysis of boranophosphoramidate to boranophosphate or reaction with orthophosphate or pyrophosphate to give the corresponding α-boranodiphosphate or α-boranotriphosphate respectively.

These steps are presented graphically in Scheme 1.

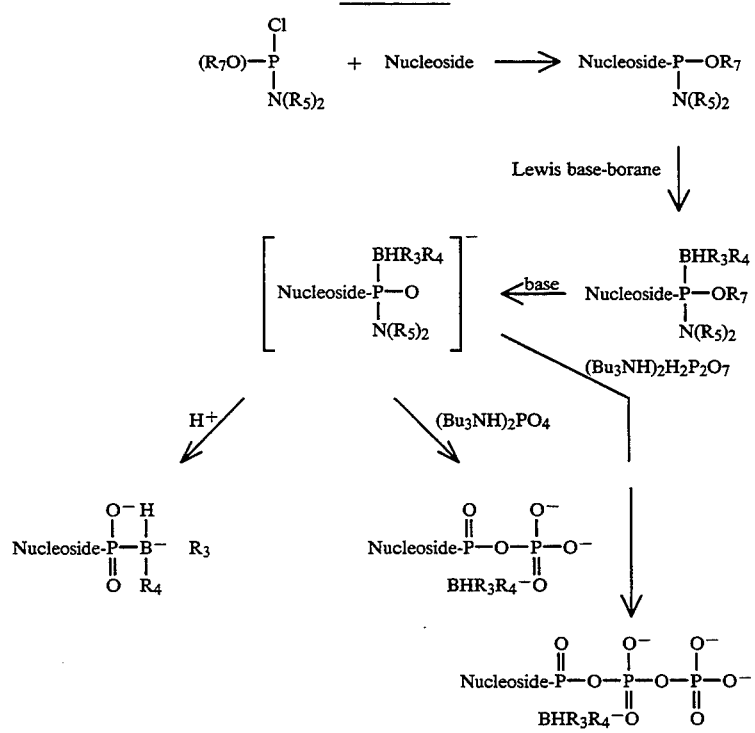

Guanosine-5'-O-(α,γ-diboranotriphosphate)
Adenosine-5'-O-(β-boranotriphosphate)
Cordycepin-5'-O-(β-boranotriphosphate)
2'-Deoxycytidine-5'-O-(γ-boranotriphosphate)

The second process which can be used for the preparation of phosphite-borane compounds of the present invention also Comprises several steps and is shown in Scheme 2.

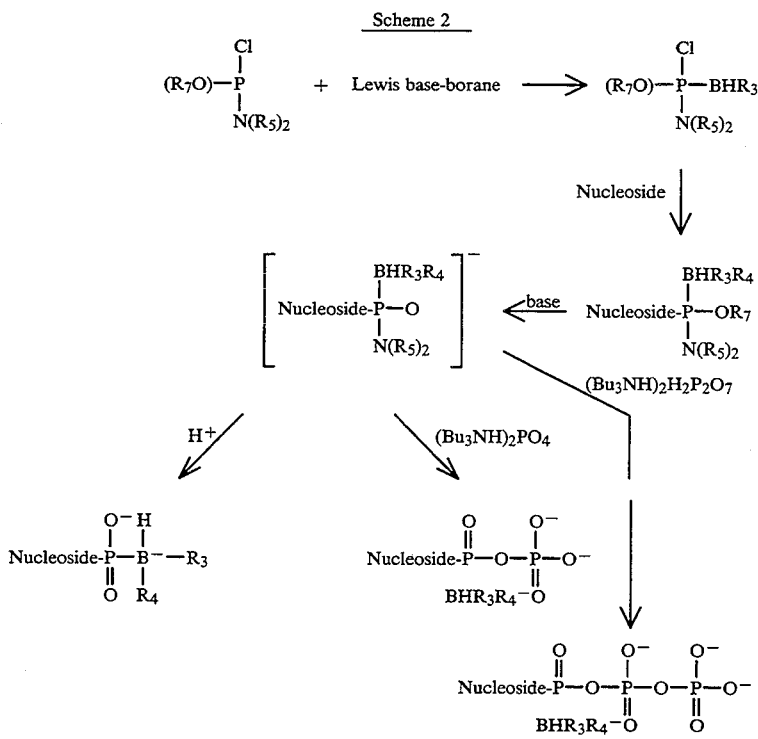

Scheme 2

The steps involved are:
a. transfer of borane from an appropriate Lewis base-borane adduct to the chloro(N,N-dialkyl)alkylphosphosramidite,
b. boranophosphorylation of the nucleoside, or an appropriate nucleoside phosphate,
c. de-esterification,
d. hydrolysis of borano-phosphoramidate to borano-phosphate or reaction with orthophosphate or pyrophosphate to give the corresponding α-boranodiphosphate or α-boranotriphosphate respectively.

The last two steps are the same as in the first process.

It should be noted that the above processes comprise individual reaction steps which can be individually utilized to prepare a full range of phosphite-borane derivatives of the present invention.

A third process which can be used for the preparation of the phosphite-borane derivatives of the invention is the condensation of a mono- or dialkylphosphite-borane derivative with a nucleoside, e.g., adenosine, guanosine, cytidine, thymidine, or uridine.

Finally, the borane ($BH_3$) derivatives of a monoalkyl- or a dialkylphosphite may be prepared in one step by base hydrolyses of a trialkylphosphite.

The compounds of the present invention have pharmaceutical activity, including anti-inflammatory, anti-hyperlipidemic, and antineoplastic activity, and are useful in treating mammals for inflammation, hyperlipidemia, and neoplasia conditions.

A method of combatting hyperlipidemia in an animal subject in need of such treatment comprises administering to the animal subject a hyperlipidemia-combatting amount of a compound of the present invention.

A method of producing an anti-inflammatory response in an animal subject in need of such treatment comprises administering to the animal subject an inflammation-combatting amount of a compound of the present invention.

A method of combatting tumors, preferably solid tumors (e.g., adenocarcinoma, bronchogenic carcinoma, osteosarcoma, epidermoid carcinoma, breast carcinoma, glioma) in an animal subject in need of such treatment comprises administering to the animal subject a tumor-combating amount of a compound of the present invention, after which the tumor preferably is exposed to thermal (low energy neutrons) radiation in an amount effective for $^{10}B$ located in the tumor (by virtue of the administration of the compound to the subject) to capture a neutron, decay, and release an alpha particle in cells of the tumor.

The above-described method of combatting tumors is a preferred modality of anti-tumor treatment; however, in addition to such utility in boron neutron capture therapy, the compounds of the present invention also have inherent anti-tumor utility.

Specifically, the compounds of the present invention exhibit cytotoxic activity against colorectal carcinoma, leukemia, osteosarcoma, glioma and bronchogenic carcinoma, by functioning as antimetabolites. Correspondingly, the compounds of the present invention facilitate a method of treating a tumor-bearing mammal, comprising of administering to such mammal a therapeutically effective amount of a phosphite-borane compound of the present invention.

Subjects to be treated by the methods of the present invention include both human and animal (e.g., bird, dog, cat, cow, horse) subjects, and are preferably mammalian subjects.

Animal subjects are administered compounds of the present invention at a daily dose of preferably at least about 0.1 mg/kg weight of the animal subject, more preferably at least about 0.5 mg/kg, and most preferably at least about 2 mg/kg. The daily dose is preferably not more than about 1000 mg/kg, more preferably not more than about 200 mg/kg, and most preferably not more than about 50 mg/kg.

As noted above, the compounds of the present invention may be administered per se or in the form of a pharmaceutically acceptable salt. When used in medicine, the salts of the compounds of the present invention should be both pharmacologically and pharmaceutically acceptable, but non-pharmaceutically acceptable salts may conveniently be used to prepare the free active compounds or pharmaceutically acceptable salts thereof and are not excluded from the scope of this invention. Where appropriate, such pharmacologically and pharmaceutically acceptable salts include, but are not limited to, those prepared from the following bases: sodium hydroxide, potassium hydroxide, ammonium hydroxide, and calcium hydroxide.

The present invention also provides pharmaceutical formulations, both for veterinary and for human medical use, which comprise the active agent (the compound of the present invention) together with one or more pharmaceutically acceptable carriers thereof and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, and in a quantity appropriate to achieve the desired daily dose.

The formulations include those suitable for oral, rectal, topical, nasal, ophthalmic, or parenteral (including subcutaneous, intramuscular and intravenous) administration. Formulations suitable for parenteral administration are preferred.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compounds into association with a liquid carrier, a finely divided solid carrier, or both, and then, if necessary, shaping the product into desired formulations.

Formulations of the present invention suitable for oral administration may be presented as discrete units such as capsules, cachets, tablets, or lozenges, each containing a predetermined amount of the active ingredient as a powder or granules; or a suspension in an aqueous liquor or a non-aqueous liquid, such as a syrup, an elixir, an emulsion, or a draught.

A tablet may be made by compression or molding, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may be added any accessory ingredient(s). Such accessory ingredient(s) may include flavorings, suitable preservatives, agents to retard crystallization of the sugar, and agents to increase the solubility of any other ingredient, such as a polyhydroxy alcohol, for example glycerol or sorbitol.

Formulations suitable for parenteral administration conveniently comprise a sterile aqueous preparation of the active compound, which preferably is isotonic with the blood of the recipient (e.g., physiological saline solution).

Nasal spray formulations comprise purified aqueous solutions of the active compound with preservative agents and isotonic agents. Such formulations are preferably adjusted to a pH and isotonic state compatible with the nasal mucous membranes.

Formulations for rectal administration may be presented as a suppository with a suitable carrier such as cocao butter, hydrogenated fats, or hydrogenated fatty carboxylic acids.

Ophthalmic formulations are prepared by a similar method to the nasal spray, except that the pH and isotonic factors are preferably adjusted to match that of the eye.

Topical formulations comprise the active compound dissolved or suspended in one or more media, such as mineral oil, petroleum, polyhydroxy alcohols, or other bases used for topical pharmaceutical formulations.

In addition to the aforementioned ingredients, the formulations of this invention may further include one or more accessory ingredient(s) selected from diluents, buffers, flavoring agents, binders, disintegrants, surface active agents, thickeners, lubricants, preservatives (including antioxidants), and the like.

The phosphite-borane compounds of the present invention, as well as other phosphite-borane compounds, may exhibit utility in anti-vital applications involving administration of such compounds to animal (human or veterinary) subjects.

The following Examples are provided to illustrate the present invention, and should not be construed as limiting the eof. Compounds are identified in the first instance by a name and a reference number, and may thereafter be identified solely by reference number, for ease of reference.

EXAMPLE 1

Diethylphosphite-borane, Sodium Salt; (compound 1)

Triethylphosphite-borane (0.70 g) was taken with 1N NaOH (20 ml) and was stirred until the oil was completely dissolved in aqueous layer. The aqueous layer was washed with $CH_2Cl_2$ (2×20 ml) and the water was removed in vacuo at room temperature. The residue was taken in ethyl acetate (~20 ml), allowed to stand for a few minutes and filtered. The filtrate was dried over anhydrous $Na_2SO_4$, filtered and the solvent was removed to give pure product yield 0.59 g, 87.2%. $^1H$ $NMR_{(D20)}$: $\delta=3.79$ 605 ppm, m, $CH_2$; 1.12 ppm, t, $CH_3$; 0.19 ppm, dq, $J_{P,H}=22\pm1$ Hz; $J_{B,H}=89\pm1$ Hz, $BH_3$. $^{11}Bnmr_{(D20)}$: $\delta=-39.9$ ppm, dq, $J_{B,H}=89\pm1$ Hz, $J_{P,B}=147$ Hz. $^{31}Pnmr_{(D20)}$: $\delta=91.1$ ppm, $J_{B,P}=146\pm2$ Hz.

EXAMPLE 2

Thymidine-5'-borano(N,N-diisopropyl)phosphoramidate; (compound 2)

3'-Acetylthymidine (284mg, 1.0 mmol), 4-dimethylaminopyridine (24.5 mg, 0.2 mmol) and diisopropylethylamine (0.7 ml, 4.0 mmol) were dissolved in anhydrous $CH_3CN$ (10 ml) under Argon. To this solution, 2-cyanoethyl N,N-diisopropylchlorophosphoramidite (0.275 ml, 1.3 mmol) was added and the mixture was stirred for 1 h. To the homogenous solution diisopropylethylamine-borane (1.7.4 ml, 10.0mmol) was added. After stirring 12 h at room temperature under argon atmosphere, the solvent was removed. The residue at evaporation was treated with a 1.5:1 mixture of $CH_3OH$/conc. $NH_4OH$ (25 ml) at RT for 5 h. After evaportation, chromatography of the residue on a QA-cellulose [$HCO_3^-$] column (1.4×50.0 cm) by using a linear gradient of aqueous $NH_4HCO_3$, pH=9.5 (2 L, 0–0.15M) and lyophilization of the appropriate fractions afforded 320 mg of a white powder of thymidine-5'-borano(N,N-diisopropyl)phosphoramidate, 2. $^1$H-NMR: δ=−0.079–0.739(2 br. m, 3H; $BH_3$), 0.973, 0.981, 0.997, 1.021, 1.105 and 1.127(6 s, 12H; $C(CH_3)_2$), 1.764 and 1.772(2 s, 3H; $CCH_3$), 2.142–2.244(m, 2H; 2'-H), 3.269–3.402(m, 2H; 5'-H), 3.720–3.795(m, 2H; N—CH), 3.973–4.027 and 4.375–4.455 (2 m, 1H; 3'-H), 6.154 and 6.230(2 t, $^3I(H,H)$=7.1 Hz, 1H; 1'-H), 7.481 and 7.519(2 d, $^4I(H,H)$=1.0 Hz, 1H, 6-H). $^{31}p[^1H]$-NMR: δ=92.2 and 93.2 (2 q, $^1J(P,B)$=147 Hz). $^{11}$B-NMR: δ=−36.8. TLC:$R_{dTMP}$=1.42.

EXAMPLE 3

Thymidine-5'-boranophosphate; (compound 3)

Compound 2 (0.16 mg) was dissolved in 0.1N aqueous trifluoroacetic acid (40 ml). After 30 min. standing at room temperature, the solution was evaporated and the residue was chromatographed on QA-cellulose [$HCO_3^-$] column (1.4×50 cm) by using a linear gradient of aqueous $NH_4HCO_3$, pH-9.5 (2 L, 0–0.2M). Lyophilization of the appropriate peak gave 93 mg (52%) of a white solid as the product in the form of monohydrate of the monoammonium salt. $^1$H-NMR: δ=0.149(dq, $^1I(B,H)$=84.0 Hz, $^2I(P,H)$=21.6 Hz, 3H; $BH_3$), 1.787(s, 3H; $CH_3$), 2.147–2.291(m, 2H; 2'-H), 3.715–3.811(m,2H; 5'-H), 3.978(unresolved, 1H; 4'-H), 4.424 (unresolved, 1H; 3'-H), 6.182(t, $^3I(I-I,H)$=6.9 Hz, 1H; 1'-H), 7.690(s, 1H; 6-H). $^{31}p[^1H]$-NMR: δ=79.3(q, $^1I(P,B)$=168 Hz). $^{11}$B-NMR: δ=−37.9(m). UV($H_2O$): $\lambda_{max}$[nm]($\epsilon$)$_{max}\lambda_{min}$[nm]=268(9100) 236[pHs 2.0 and 7.0], 268(7500)244[pH 11.0]. MS(electrospray ionization, 3000 V): m/z 321 [3+3H]$^+$.TLC:$R_{dTMP}$=1.25. RP-HPLC($C_{18}$, A:0.02M $KH_2PO_4$, B:$CH_3CN$, 0–25% B/5 min, 3.0 mlmin$^{-1}$, $t_R$=4.98 min).

EXAMPLE 4

Thimidine-5'-(α-borano-triphosphate); (compound 4)

Compound 1 (160 mg) was reacted with 0.5 M ($Bu_3NH)_2H_2P_2O_7$ in DMF (4.0 ml) with the exclusion of atmospheric moisture at 55° C. for 4 h. The mixture was poured into 0.1M aqueous $NH_4HCO_3$ (40 ml) at room temperature, then separated on a DEAE-cellulose [$HCO_3^-$] column [2.1×52.0 cm] by using a linear gradient of aqueous $NH_4HCO_3$ (3 L, 0.1–0.3M, 10° C.). Appropriate fractions were combined and lyophilized to give 61.2 mg (30%) of the product as a white solid. $^1$H-NMR: δ=−0.249–0.804(2 br.m, 3H; $BH_3$), 1.780 and 1.788(2s, 3H; CH3), 2.194–2.216(m, 2H; 2'-H), 3.961–4.168(2 m, 3H; 4'-H, 5'-H), 4.4494.497 and 4.536–4.584(2 m, 1H; 3'-H), 6.190(t, $^3I(H,H)$=6.7 Hz, 1H; 1'-H), 7.571 and 7.557(2s, 1H; H-6). $^{31}$ p[$^1$H]-NMR: δ=−21.4(t, $^2j(p,p$=21.4 Hz, 1P, p$^2$), −5.50(unresolved, 1P; p$^3$), 82–84(br. m, 1P; p$^1$) $^{11}$B-NMR: δ=−38.6(m, $^1j$ B,P)=137 Hz, $^1I(B,H)$=92 Hz). MS: m/z 498 [4+4H+$NH_4$]. TLC: $R_{dTTP}$=1.40. RP-HPLC($C_{18}$, A:0.2M triethylammonium acetate, pH=7.5, B:methanol, 0–10% B/20 min, then 10% B/10 min, 4.0 mlmin−1, $t_R$=20.91(60%) and 24.57(40%) min.

EXAMPLE 5

Adenosine 5'-boranophosphate; (compound 5)

To a 1.0M solution of THF-borane in THF (5.0 ml)(N,N-diisopropylamino)(cyanoethyl)phosphoramidic chloride (300 μl), 1.4 mmol was added under argon. After 10 min. stirring at RT, the solution was evaporated. The oily residue at evaporation was dissolved in acetonitrile (5 ml), and the slightly opalescent solution was added to a mixture of 2',3'-di-O-acetyladenosine (351 mg, 1.0 mmol), 4-dimethylaminopyridine (24.5 mg, 0.2 mmol) and diisopropylethylamine (0.7 ml, 4.0 mmol) in acetonitrile (5 ml). The reaction mixture was stirred with the exclusion of atmospheric moisture at RT for 3 h. Conc. $NH_4OH$ (10 ml) was poured into the pale yellow solution under stirring. The solution was set aside at RT overnight, then evaporated to dryness. The evaporational residue was purified on a QA-cellulose [$HCO_{3-}$] column (1.4×50.0 cm) by using a linear gradiant of aqueous $NH_4HCO_3$, pH=9.5 (2 L, 0–0.15M) to give 138.0 mg of crude adenosine 5'borano-(N,N-diisopropyl)phosphoramidate. The crude product was treated with 0.1M aqueous trifluoroacetic acid (25 ml) at RT for 30 min. The solution was evaporated and the residue was chromatographed on a QA-cellulose[$HCO_3^-$] column (1.4×50.0 cm) by using a linear gradient of aqueous $NH_4HCO_3$, pH 9.5 (2 L, 0–0.25M). Appropriate fractions were pooled, concentrated to a small volume then lyophilized to give 49 mg (13%) of a white solid of the monoammonium salt of adenosine of 5'-boranophosphate. UV, $\lambda_{max}$[nm] 258 (pH 2.0), 260 (pHs 7.0 and 11.0), $\lambda_{min}$[nm] 232 (pH 2.0), 228 (pHs 7.0 and 11.0). $^{31}$P-NMR: δ(ppm) 78.79 (q, $^1I_{BP}$=170 Hz) $^{11}$B-NMR: δ(ppm)−37 8 sextet, overlapping quartets of a doublet, $^1I_{BP}$=168 Hz, $^1I_{BH}$=85 Hz).

EXAMPLE 6

Synthesis of 3'-O-acetylthymidine-5'-diethylphosphite-cyanoborane; (compound 6)

3'-Acetylthymidine (0.35 g, 1.24 mmol), diethylphosphite-cyanoborane (0.22 g, 1.24 mmol) and dicyclohexylcarbodiimide, DCC, (2.48 mmol) were taken in anhydrous acetonitrile and the mixture was stirred at room temperature for 48 hours. To the mixture another 2.48 mmol of DCC was added and the mixture was stirred for another 24 hours. After filtration to remove insoluble materials, the solvent was removed under reduced pressure. The residue was taken in dichloromethane (40 ml) and was washed with water (5×30 ml). The organic layer was dried, filtered, and concentrated under reduced pressure. The residue was purified by flash chromatography on silica gel using EtOAc: hexane (9:1). Yield was 0.225 g, 46.5%. 'H nmr (CDCl3): δ=1.41,t and 1.44,t, 2CH3's (OEt); 1.00–1.80, v. br., $BH_2$; 1.98 ppm, s and 1.99 ppm, s, $CH_3$ (for two diastereomers); 2.13 ppm, s, $CH_3(OAc)$; 2.30–2.41, m, 2'$CH_2$; 4.15 ppm, m, 4'H; 4.25 ppm, m, $CH_2$'s (OEt); 4.29–4.47 ppm, m, 5'$CH_2$; 5.26 ppm, br., 3'H; 6.43 ppm, m, 1'H; 7.36 ppm, 2 singlets, H6 (for two diastereomers) and 9.20 ppm, s, NH. $^{13}$C nmr (CDCl3): δ=12.35 ppm, s, $CH_3(C_5)$; 16.02 and 16.10 ppm, 2 doublets, $CH_3$'s (OEt); 20.80 ppm, s, $CH_3(OAc)$; 36.54 ppm, s, 2'$CH_2$; 65.19 and 65.33 ppm, 2 doublets, $CH_2$'s (OEt); 65.94 ppm, d, 5'CH$_2$; 74.21 ppm, s, 3'CH; 82.41 ppm, d, 4'CH; 84.06 ppm, s, 1'CH; 112.10 ppm, C5; 134.69 ppm, s. C6; 150.61 ppm, s, C2; 163.61 ppm, s, C4; 170.74 ppm, s, CO(OAc). $^{-}$P nmr (CDCl$_3$): $\delta = 94.26$ ppm, br.q., $^1J_{B,P} = 156$ Hz (based on inner two peaks). FAB MS: MH+: 444.3. Analysis, calculated: % C, 46.07; % H, 6.14; and % N, 9.48. Found: % C, 46.21; % H, 5.94 and % N, 9.37.

EXAMPLE 7

Incorporation of Thymidine-5'-($\alpha$-borano-triphosphate) into Oligonucleotides Using Polymerases In vitro incorporation of thymidine-5'-$\alpha$-boranotriphosphate into DNA was studied using two different polymerases; Sequenase (a modified T7 DNA polymerase; from USB) and the Klenow fragment of DNA polymerase I (from New England Biolabs). Both polymerases appeared to readily accept the boranophosphate nucleotide. The experiment was carried out using a 17-mer primer extended against a 25-mer template containing a single dA coding site. Extension was performed at 37° C. for 15 minutes in the presence of 100 $\mu$M dATP, dGTP, dCTP and either 100 $\mu$M dTTP or 100 $\alpha$-borano-dTTP. The extension products were separated by denaturing PAGE. Autoradiography showed that the primer was extended to completion without any detectable pause in the presence of either normal or boronated dTTP.

(Minowada, J., et al, *J. Nat. Cancer Int.* 1972, 49, 891–895); colorectal adenocarcinoma SW480 (Liebovitz, A., et al, *Cancer Res.* 1976, 36, 4562–4569); lung bronchogenic MB-9812 (Aaronson, S. A., et al, *Expt. Cell Res.* 1970, 61, 1–5); osteosarcoma TE418 (Smith, H. S., et al, *Int. J. Cancer* 1976, 17, 219–234); KB epidermoid nasal pharynx (Geran, R. I., et al, Ibid.; Eagle, H., *Proc. Soc. Expt. Biol.* 1955, 89, 362–364); Hala-S$^3$ suspended cervical carcinoma (Puck, T. T., et al, *J. Exp. Med.* 1956, 103, 273–283); glioma EH 118 Mg (Nelson-Rees, W. A., et al, *Int. J. Cancer* 1975, 16, 74–82) and Ileum HCT Colon.

The protocol used to assess cytotoxicity was that of Geran, et al, *Cancer Chemotherapy Reports*, 1972, 3, 7–9. Standards were determined in each cell line. Values are expressed for the cytotoxicity of the drug as ED$_{50}$ in $\mu$g/ml, i.e., the concentration which inhibits 50% of the cell growth determined by the trypan blue exclusion technique. Solid tumor cytotoxicity was determined by the method of Huang, E. S., et al, *J. Pharm. Sci.* 1972, 61, 108–110. Ehrlich ascites carcinoma in vivo tumor screens were conducted in CF$_1$ male mice $\approx 28$ g) with test drugs at 8 mg/kg/day I.P. by the method of Geran, et al (supra). 6-Mercaptopurine was used as an internal standard.

The results of the cytotoxicity tests are set out in Table 1 below for compounds 1, 3, 4, and 6, as well as 5FU, araC, hydroxyurea, cycloleucine, and 6MP.

TABLE 1

| | | The Cytotoxic and Antitumor Activity of Phosphite-boranes | | | | | | | | |
|---|---|---|---|---|---|---|---|---|---|---|
| | | ED$_{50}$ ($\mu$g/ml) | | | | | | | | |
| Compound | % Inhibition in vivo Ehrlich Ascites | L$_{1210}$ | Tmolt$_3$ | Colon SW480 | KB | HeLa—S$^3$ | Osteo-Sarcoma | Lung bronchogenic | Glioma | Ileum HCT Colon |
| 1 | | | | | | | | | | |
| 3 | | 2.35 | 5.21 | | | | 6.28 | | | 7.64 |
| 4 | | 2.52 | 3.49 | | | | | | | |
| 6 | 48 | 3.63 | 2.83 | 2.57 | 3.62 | 2.67 | 5.51 | 4.16 | 5.66 | |
| 5FU | | 1.41 | 2.14 | 3.09 | 1.25 | 2.47 | — | 5.64 | 1.28 | |
| Ara C | | 2.76 | 2.67 | 3.42 | 2.54 | 2.13 | — | 7.24 | 1.88 | |
| Hydroxyurea | | 2.67 | 3.18 | 4.74 | 5.29 | 1.96 | 7.57 | 7.33 | 2.27 | |
| Cycloleucine | | 3.08 | 2.38 | 3.81 | 5.74 | 2.38 | 6.18 | 4.36 | 5.89 | |
| 6MP | 99 | | | | | | | | | |

EXAMPLE 8

Inhibition of Alkaline Phosphatase Activity 2.0 absorbance (A260) units of thymidine-5'-boranophosphate and 0.5 units of the enzyme alkaline phosphatase from *E. coli* were taken in 40 ml of 0.1M Na$_2$CO$_3$—NaHCO$_3$, pH 10.4 and the reaction was followed by tlc. No hydrolysis was observed even after 4 h. The thymidine-5'-phosphate, which does not have boron, is completely hydrolyzed in <1 h.

EXAMPLE 9

Cytotoxic Activity of Phosphite-borane Compounds

The compounds prepared in accordance with the preceding Examples were tested for cytotoxic activity, by preparing a 1 mM solution of the adduct in 0.05% Tween® 80/H$_2$O solution by homogenization. The resulting drug solutions were sterilized by passage through an Acrodisc 45 $\mu$M sterilizer.

The following cell lines were maintained in accordance with literature techniques (literature source indicated parenthetically after identification of the cell line): murine L$_{1210}$ lymphoid leukemia (Geran, R. I., et al, *Cancer Chemotherapy Reports* 1972, 3, 7–9); human Tmolt$_3$ acute lymphoblastic T cell leukemia

EXAMPLE 10

Hypolipidemic Activity of Phosphite-borane Compounds

Test compounds (3 and 6) were suspended in an aqueous 1% carboxymethylcellulose solution, homogenized, and administered to CF1 male mice ($\approx 25$ g) intraperitoneally for 16 days. On days 9 and 16, blood was obtained by tail vein bleeding, and the serum was separated by centrifugation for 3 minutes. The serum cholesterol levels were determined by a modification of the Liebermann-Burchard reaction (Ness, A. T., et al, *Clin. Chim. Acta.* 1964, 10, 229–237). Serum was also analyzed for triglyceride content by a commercial kit (BioDynamics/bmc) using a BMC single vial triglycerides colorimetric method 348201. Food and water were available ad libitum for animals in the experiments.

In vitro enzymatic studies were determined using 10% homogenates of CF$_1$ male mouse liver with compound 6. The enzyme activities were determined by the following literature procedures (Chapman, J. M., Jr., et al, *J Med. Chem.* 1979, 22, 1399–1402); acetyl coenzyme A synthetase (Hoffmann, G., et al, *Anal. Biochem.* 1978, 84, 441–448); 3-hydroxy-3-methylglutaryl coenzyme A reductase (Haven, G. T., et al, *J. Biochem.* 1969, 65, 171–175); acetyl coenzyme A carboxylase activity (Greenspan, M. D., et al, *J. Biol. Chem.* 1968, 243, 6373–6280); sn-glycerol-3-phosphate acyl transferase activity (Lamb, R. G., et al, *Biochim. Biophys. Acta.* 1977, 489, 318–329); phosphatidylate phosphohydrolase activity (Mavis, R. D., et al, *J. Lipid Res.* 1978, 19, 467–477); acyl CoA cholesterol acyl transferase (Balasubramaniam, S., et al, *Eur. J. Biochem.* 1978, 90, 377–383); and Squalene cyclase.

The results of the foregoing analytical tests are set out below in Table 2 ("The Hypolipidemic Activity of Phosphite-boranes in $CF_1$ Mice at 8 mg/kg/day I.P."), and Table 3 ("The Effects of Phosphite-boranes on Enzyme Activities of Lipid Metabolism of $CF_1$ Mice").

TABLE 2

The hypolipidemic activity of phosphite-boranes in $CF_1$ mice at 8 mg/kg/day ip.

| [N = 6] | Percent of Control | | |
|---|---|---|---|
| | Serum Cholesterol | | Serum Triglycerides |
| | Day 9 | Day 16 | Day 16 |
| Control | 100 ± 6 | 100 ± 5 | 100 ± 7 |
| Compound | | | |
| 3 | 54 | 41 | 60 |
| 6 | 77 | 48 | 73 |

TABLE 3

Effect of phosphite-boranes on mouse hepatic enzyme activities $IC_{50} \times 10^5 M$

| Enzyme | Compound 6 |
|---|---|
| Acetyl CoA Synthetase | 0.49 |
| HMG CoA Reductase | 1.62 |
| Acyl CoA Cholesterol Acyl Transferase | 1.22 |
| Squalene Cyclase | 0.51 |
| Acetyl CoA Carboxylase | 1.11 |
| sn-Glycerol-3-Phosphate Acyl Transferase | 1.47 |
| Phosphatidylate Phosphohydrolase | 0.91 |

Thus, the phosphorus-boron derivatives of the present invention have been shown to be potent hypolipidemic agents in rodents, significantly lowering both serum cholesterol and serum triglycerides in mice at a low dose of 8 mg/kg/day, which is not true for many commercially available hypolipidemic agents.

These compounds reduced the activities of hepatic de novo enzymes involved in the early cytoplasmic synthesis of cholesterol, i.e. acetyl CoA synthetase. The rate limiting enzyme for cholesterol synthesis, HMG CoA reductase, was also significantly inhibited. Enzymes involved in triglyceride synthesis, e.g. acetyl CoA carboxylase, regulatory enzymes phosphatidylate phosphohydrolase and sn-glycerol-3-phosphate acyl transferase were also inhibited.

EXAMPLE 11

Anti-inflammatory Activity of Phosphite-Borane Compounds $CF_1$ male mice ($\approx 25$ g) were administered test drugs at 8 mg/kg in 0.05% Tween ® 80-$H_2O$ intraperitoneally 3 hr. and again 30 min. prior to the injection of 0.2 ml of 1% carrageenan in 0.9% saline into the plantar surface of the right hind foot. Saline was injected into the left hind foot which serves as a base line. After 3 hours, both feet were excised at the tibiotarsal (ankle)s joint according to the modified method of Winter (Winter et al, *Proc. Soc. Exp. Biol. Med.* 1962, 111, 544–547, and Hendershot and Forsaith, *J. Pharmacol. Exp. Ther.* 1970, 175, 435–442). The control mice afforded a 78±3 mg increase in the paw weight. Data are presented in Table 4 below.

TABLE 4

Anti-inflammatory activity of compound 1 & 6 in $CF_1$ mice at 8 mg/kg.

| Compound | Percent of Control (Induced edema) |
|---|---|
| 1 | |
| 6 | 73.9 |

While the invention has been described herein with reference to illustrative compounds and specific embodiments of the invention, it will be appreciated that numerous variations, modifications, and other embodiments are possible, and accordingly, all such variations, modifications, and embodiments are to be regarded as being within the spirit and scope of the invention.

What is claimed is:

1. A pharmaceutical composition comprising a therapeutically effective amount of a phosphite-borane compound corresponding to the formula:

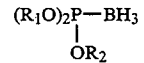

where:
  each $R_1$ is independently selected from H, $C_1$–$C_{20}$ alkyl, alkylaryl, aryl, and trialkylsilyl, with the proviso that both $R_1$ groups cannot simultaneously be H; and $R_2$ is selected from H, monovalent cations, and $N(R_3^+)_4$ wherein $R_3$ is independently selected from H, and $C_1$–$C_{20}$ alkyl; and
  a pharmaceutically acceptable carrier, wherein said pharmaceutical composition is in a form selected from the group consisting of capsules, cachets, tablets, lozenges, powder or granules in aqueous liquor, syrup, elixir, emulsion, draught, isotonic physiological solution, nasal spray formulation, rectal formulation, ophthalmic formulation, and topical formulation.

2. The pharmaceutical composition according to claim 1, wherein the therapeutically effective amount is a hyperlipidemia-combating amount.

3. The pharmaceutical composition according to claim 1, wherein the therapeutically effective amount is an antineoplastic amount.

4. The pharmaceutical composition according to claim 1, wherein the therapeutically effective amount is an anti-inflammatory amount.

* * * * *